US009488609B2

(12) United States Patent
Khosravani

(10) Patent No.: US 9,488,609 B2
(45) Date of Patent: Nov. 8, 2016

(54) DETERMINATION OF ANISOTROPIC CONDUCTION CHARACTERISTICS

(71) Applicant: The Boeing Company, Chicago, IL (US)

(72) Inventor: Shahriar Khosravani, Everett, WA (US)

(73) Assignee: The Boeing Company, Chicago, IL (US)

( * ) Notice: Subject to any disclaimer, the term of this patent is extended or adjusted under 35 U.S.C. 154(b) by 262 days.

(21) Appl. No.: 14/174,768

(22) Filed: Feb. 6, 2014

(65) Prior Publication Data

US 2015/0219577 A1    Aug. 6, 2015

(51) Int. Cl.
*G01N 27/04* (2006.01)
*G01N 27/20* (2006.01)

(52) U.S. Cl.
CPC ............ *G01N 27/041* (2013.01); *G01N 27/20* (2013.01)

(58) Field of Classification Search
USPC ...... 324/693, 663, 691, 71.1, 722, 649, 600, 324/615, 638, 549, 439, 639; 977/888, 890, 977/891; 73/802, 865.8; 361/218
See application file for complete search history.

(56) References Cited

U.S. PATENT DOCUMENTS

| 5,095,273 | A | * | 3/1992 | Kennedy | ................ G01N 33/24 324/376 |
|---|---|---|---|---|---|
| 5,171,419 | A | | 12/1992 | Wheeler et al. | |
| 6,297,155 | B1 | * | 10/2001 | Simpson | ............. H01L 21/2885 257/E21.175 |
| 2010/0263898 | A1 | * | 10/2010 | Hebert | ...................... B64C 1/12 174/2 |

FOREIGN PATENT DOCUMENTS

EP         0269850 A1 *  6/1988   ............ D01F 11/127

OTHER PUBLICATIONS

Office Action for Canadian Application No. 2,871,035; Date of Mailing: Jan. 7, 2016; Canadian Intellectual Property Office, (3 pages).
Lightning Strike Protection for Carbon Fiber Aircraft—DEXMET; Society for the Advancement of Materials Process Engineering (SAMPE), and presented at the SAMPE conference in Baltimore, MD, Jun. 2007.
Kawakami; Lightning Strike Induced Damage Mechanisms of Carbon Fiber Composites; University of Washington; Nov. 28, 2011; UMI Dissertation Publishing; ProQuest information and Learning, 300 North Zeeb Road, Ann Arbor, MI 48106-1346.

* cited by examiner

*Primary Examiner* — Nasima Monsur
(74) *Attorney, Agent, or Firm* — Toler Law Group, PC

(57) ABSTRACT

A method includes applying a current to a specimen to deposit a material on the specimen. The method also includes determining a quantity of the material deposited at multiple locations of the specimen and determining anisotropic conductive characteristics of the specimen based on the quantity of the material deposited at the multiple locations on the specimen.

20 Claims, 14 Drawing Sheets

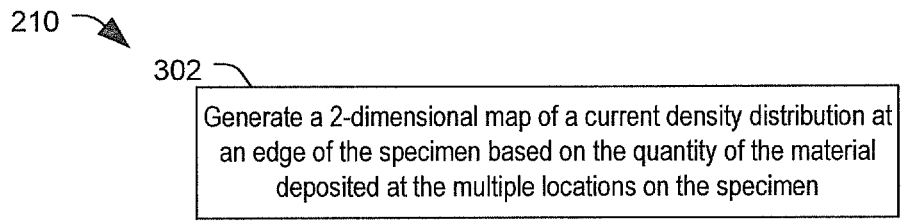
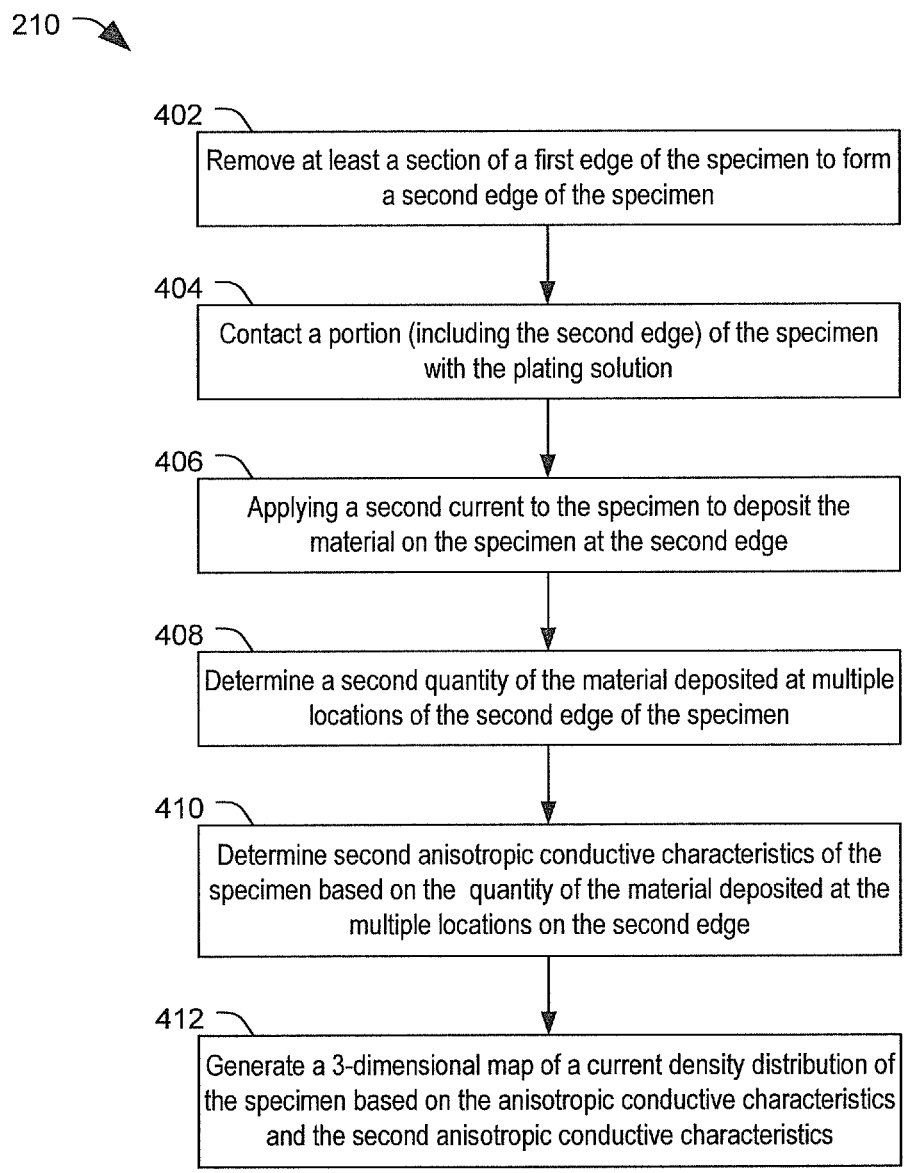

US 9,488,609 B2

DETERMINATION OF ANISOTROPIC CONDUCTION CHARACTERISTICS

FIELD OF THE DISCLOSURE

The present disclosure is generally related to determination of anisotropic conduction characteristics.

BACKGROUND

Composite materials are being used in an increasing variety of applications. For example, composite materials are being used to replace metals in many applications. Using composite materials to replace metals can have significant benefits, such as reduced weight. However, there are often differences between material properties of metals and material properties of composite materials used to replace them. For example, certain material properties of composite materials may be anisotropic. To illustrate, a composite material may have electrical properties that vary by location or direction.

Anisotropic electrical properties can make replacing metals with composite materials problematic. For example, commercial aircraft have traditionally used metal skins. Metal skins provide more or less uniform electrical properties, which can help distribute charge evenly in the event of a lightning strike. Forming aircraft skins of composite materials can reduce aircraft weight; however, the composite materials tend to conduct anisotropically. Anisotropic conduction may lead to localized hotspots in the event of a lightning strike, which can cause significant damage, such as delamination of the composite material.

Aircraft manufacturers and regulatory agencies use considerable care in selecting and testing composite materials used for aircraft skins. Generally, testing is performed by applying simulated lightning strikes to assemblies of components including composite materials (e.g., a composite panel with metal connectors). Testing a large variety of materials, assembly processes, and other components (e.g., connectors) in this manner is time consuming and expensive.

SUMMARY

In a particular embodiment, a method for determining anisotropic conductive characteristics of a specimen includes applying a current to a specimen to deposit a material on the specimen. The method also includes determining a quantity of the material deposited at multiple locations of the specimen and determining anisotropic conductive characteristics of the specimen based on the quantity of the material deposited at the multiple locations on the specimen. The method further includes predicting performance of a component formed of the specimen material based on the anisotropic conductive characteristics of the specimen.

In another particular embodiment, a method for predicting performance of a component when subjected to a lightning strike includes contacting a first edge of a specimen with a plating solution. The specimen includes a plurality of fibers and ends of at least a subset of fibers of the plurality of fibers are exposed to the plating solution at the first edge. The method also includes applying a current to the specimen at a location removed from the first edge, where the current is conducted to the plating solution via the multiple fibers and the first edge. The method further includes determining a quantity of material deposited at multiple locations of the first edge responsive to the current. The method also includes generating a 2-dimensional map of a current density distribution at the first edge of the specimen based on the quantity of the material deposited at the multiple locations on the first edge. The method further includes predicting performance of a component formed of the specimen material when the component is subjected to a lightning strike based on the current density distribution.

In another particular embodiment, a method for predicting performance of a component when subjected to a lightning strike includes preparing a first specimen of fiber composite material by coupling a first connector to the first specimen using a first assembly process. The method also includes applying a first current to the first specimen via the first connector to deposit a material on the first specimen and determining a quantity of the material deposited at multiple locations of the first specimen responsive to the first current. The method further includes preparing a second specimen of the fiber composite material by coupling a second connector to the second specimen using a second assembly process. The method also includes applying a second current to the second specimen via the second connector to deposit the material on the second specimen and determining a second quantity of the material deposited at multiple locations of the second specimen responsive to the second current. The method further includes selecting a connector, an assembly process, or both, based on a comparison of the quantity of the material deposited at multiple locations of the first specimen responsive to the first current and the quantity of the material deposited at multiple locations of the second specimen responsive to the second current. The method further includes predicting performance of a component formed of the specimen material when the component is subjected to a lightning strike based on the comparison of the material deposited on the first and second specimens.

BRIEF DESCRIPTION OF THE DRAWINGS

FIG. 3 is a flow chart of a first embodiment of a method of generating or gathering additional data from FIG. 2;

FIG. 4 is a flow chart of a second embodiment of a method of generating or gathering additional data from FIG. 2;

DETAILED DESCRIPTION

Fastener/composite material interfaces are of particular interest when determining performance of an assembly during a lightning strike because regions around fasteners may be exposed to very high currents. Average conductivity measurements for the assembly may not be very informative of how the assembly will respond to a very high current due to the anisotropic electrical properties of the composite material. For example, assemblies that use fasteners selected from a group of fasteners with the same installation specifications and the same average conductivity may exhibit a relatively large variation in lightning strike performance (e.g., due to fastener/composite material interface differences). Also, different assembly processes can affect lighting strike performance. For example, an interference fit fastener interface may have better lightning strike characteristics than a clearance fit fastener interface for the same size fastener. Current density distribution in an area around a fastener may be a better indicator of lightning strike performance of an assembly than average conductivity. The current density distribution may be estimated or mapped by using an electrochemical deposition process, as described further below.

Figure 1:
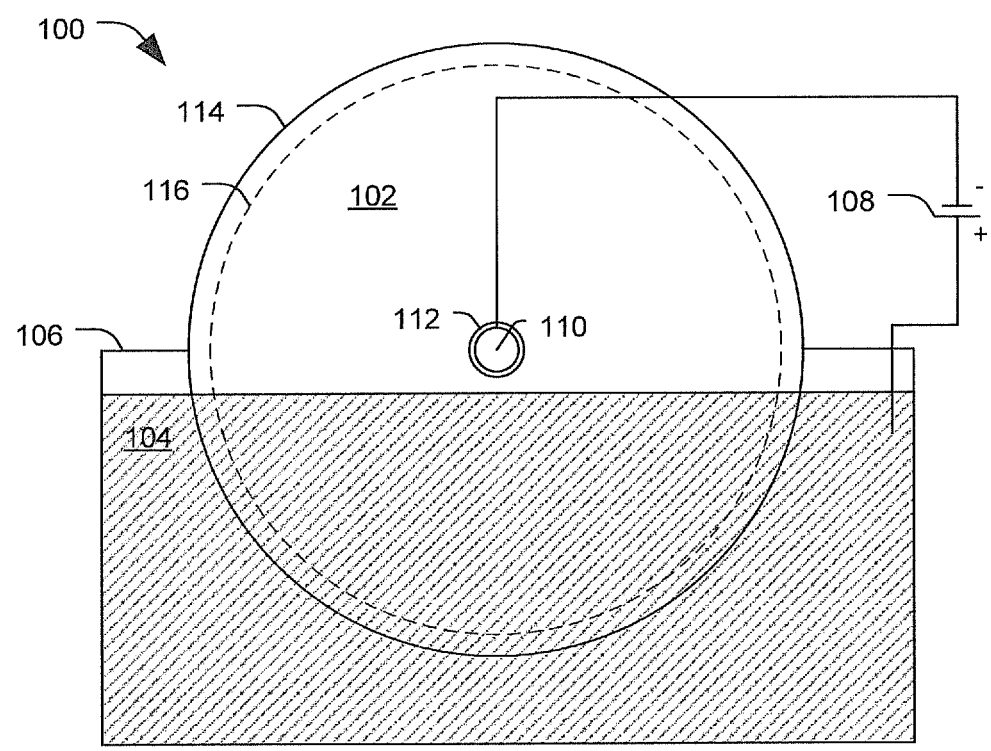
FIG. 1 is a diagram of a particular embodiment of system for evaluating anisotropic conductive characteristics of a specimen.

FIG. 1 is a diagram of a particular embodiment of system 100 for evaluating anisotropic conductive characteristics of a specimen 102. The specimen 102 may include or be formed of a composite material, such as a carbon fiber reinforced polymer (CFRP) or another composite material that includes conductive fibers in a matrix. In a particular embodiment, the composite material includes multiple fiber plies arranged in different orientations bonded together by a polymer matrix. As described further below, material may be deposited on the specimen 102 to evaluate anisotropic conductive characteristics of a specimen 102.

The specimen 102 may be prepared by coupling a connector 110 to the composite material. The connector 110 may be coupled to the composite material via a connector interface 112. Depending on an assembly process used, the connector interface 112 may be simple or complex. Examples of simple connector interfaces include interference connector interfaces (e.g., where the connector 110 in direct physical contact with the composite material) and a clearance connector interface (e.g., where there is a gap between the connector 110 and the composite material). Examples of more complex connector interfaces include connector interfaces that use an intervening material (e.g., an adhesive, a sleeve, a conductive aide, other materials, or a combination thereof) between the connector 110 and the composite material. Different connectors and different assembly processes may be used to prepare different specimens in order to compare effects of the different connectors and different assembly processes.

After the connector 110 is coupled to the specimen 102, material may be deposited on the specimen using an electrochemical deposition process, such as electroplating. For example, a portion of the specimen 102 may be contacted with a plating solution 104 in a plating bath 106. The connector 110 may be coupled to a power supply 108. The power supply 108 may also be coupled to an electrode that is in contact with the plating solution 104. The power supply 108 may apply a current to the specimen 102 via the connector 110. The fibers of the specimen 102 (e.g., carbon fibers), and possibly to a lesser extent a matrix of the specimen 102, may conduct the current to the plating solution 104. A plating material (such as copper) may be deposited on the specimen 102 in response to the current.

The quantity of plating material deposited at any particular location of the specimen 102 is directly related to the amount of current conducted to the plating solution at the particular location. For example, when the plating material is copper, more copper may be deposited on the specimen 102 at a first location than at a second location as a result of the first location of the specimen 102 conducting more current than the second location the specimen 102. In a particular embodiment, different portions of the specimen 102 may conduct current differently as a result of orientation and arrangement of fibers in the specimen. For example, fibers within the specimen 102 may be arranged in fiber plies. In each fiber ply, the fibers are oriented primarily in one or more directions. To illustrate, the fibers may be arranged in a two-directional weave. Different plies may be oriented in different directions. However, even in this arrangement, the fibers of the specimen 102 as a whole may not be uniformly arranged in every direction. To illustrate, when the specimen 102 is circular, fibers exposed at a first edge 114 may not be distributed uniformly. Additionally, certain of the exposed fibers may intersect directly with the connector 110 while other fibers do not. Thus, when the current is conducted from the connector 110 to the plating solution 104, the current is conducted anisotropically by the specimen, resulting in non-uniform deposition of the plating material on the specimen 102.

The quantity of plating material deposited at a particular location can be estimated (e.g., visually) or may be measured. In a particular embodiment, the mass of plating material deposited at a particular location may be measured based on height of the deposited material, as described below.

Mass deposited in an electrochemical process (e.g., electrolysis) may be expressed as:

$$m = \left(\frac{Q}{F}\right)\left(\frac{M}{z}\right) \quad \text{Equation (1)}$$

where m is the mass (e.g., in grams) of a substance (e.g., the plating material) liberated at an electrode (e.g., a fiber of the specimen 102 in FIG. 1), Q is the total electric charge passed through the substance, F is the Faraday constant (e.g., 96485 C mol-1); M is the molar mass of the substance, and z is the valence number of ions of the substance (electrons transferred per ion).

For a particular waveform and for a particular duration, the total delivered charge during a particular duration may be determined by:

$$Q = \int_0^t I(t)dt \quad \text{Equation (2)}$$

where t is the duration (e.g., in seconds), Q is the total electric charge passed through the substance, and I(t) is the current waveform (e.g., current as a function of time). For electrolysis processes, the waveform has fixed polarity. For example, the current waveform may be a DC waveform. For a DC waveform with a fixed current level of $I_0$, the total delivered charge to the electrodes is:

$$Q = I_0 t \quad \text{Equation (3)}$$

Thus, simplifying and substituting Equation 3 into Equation 1, the change in mass of the material at a particular fiber, j, over time may be expressed as:

$$\Delta m = \left(\frac{I_j}{F}\right)\left(\frac{M}{z}\right) \cdot \Delta t \quad \text{Equation (4)}$$

For fibers with a generally circular cross-section, it is reasonable to assume that the growth of deposited material is spherical symmetric due to spatial symmetry of ionic movement in the electrolyte. That is, at the end of a single fiber, the material may be assumed to be deposited in a roughly spherical shape. Assuming none of the material is initially present on the fiber, the mass of material deposited at a particular fiber may be related to the height of the deposited material above the fiber by:

$$\Delta m = \frac{4}{3}\pi\rho((D_f/2)^2 + h_2^2)^{\frac{3}{2}} \quad \text{Equation (5)}$$

where $\Delta m$ is change in mass of the material (e.g., accumulation of the material in terms of mass), $\rho$ is density of the material, $D_f$ is the diameter of the fiber, and $h_2$ is final height of the material above the fiber (where the initial height, $h_1$, is zero since none of the material was initially present on the fiber).

Substituting Equation (4) into Equation (5) and solving for $$I_j = \frac{4\pi\rho \cdot z}{3M\Delta t}((D_f/2)^2 + h_j^2)^{\frac{3}{2}} \quad \text{Equation (6)}$$

Equation (6) may be used to determine current flow through a particular fiber based on height of plating material deposited on the particular fiber. For example, after depositing material on the specimen 102, height of material deposited on particular fibers or in particular regions may be measured using a height-sensitive calibrated optical microscope (e.g., a differential interference contrast microscope). The deposited height can be used to generate a 2-dimensional map current density of at least a portion of the first edge 114 of the specimen 102.

After measuring or estimating the current density distribution at the portion of the first edge 114, the first edge 114 may be removed (e.g., cut away) to reveal a second edge 116. The deposition process may be repeated for the second edge 116 to generate a current density distribution of a portion of the second edge 116. The process of depositing material on new edges (e.g., smaller and smaller diameter portions of the specimen 102) may be used to generate a 3-dimensional map of the current density distribution of the specimen 102. Thus, anisotropic conductive characteristics of the specimen 102 can be measured with good accuracy and at relatively low cost.

The process described above may be used to select materials for use (e.g., to form an assembly) or for further testing. For example, the process described above may be repeated for different specimens to enable comparison of the specimens. The specimens may use different composite materials, different fasteners, different fastener interfaces (or assembly processes), or a combination thereof. Of a set of tested specimens, a specimen with a more uniform current distribution would be expected to provide better lightning strike performance than a specimen with a less uniform current distribution.

Since lightning strike testing can be expensive and time consuming, only a specimen or set of specimens that have the most uniform current distribution may be used to form assemblies that are subjected to lightning strike testing. Accordingly, a large sampling of specimens can be pre-screens using the process described above, and only a few promising specimens can be subjected to the more expensive lightning testing.

The information regarding current density distribution can also be used for purposes other than pre-screening for lightning strike testing, such as to determine basic anisotropic electrical properties of the specimen 102. For example, the process described above may be repeated for multiple, substantially identical specimens (e.g., specimens formed of the same type of composite material, the same type of connect and the same type of connector interface). Different voltages of the power supply 108 may be used to test the substantially identical specimens. For many composite materials, a current-voltage relationship is non-linear (e.g., as voltages increase, eventually a matrix of the composite material may be experience dielectric breakdown). Thus, by using different voltages, the current-voltage relationship may be evaluated for the composite material.

Figure 2:
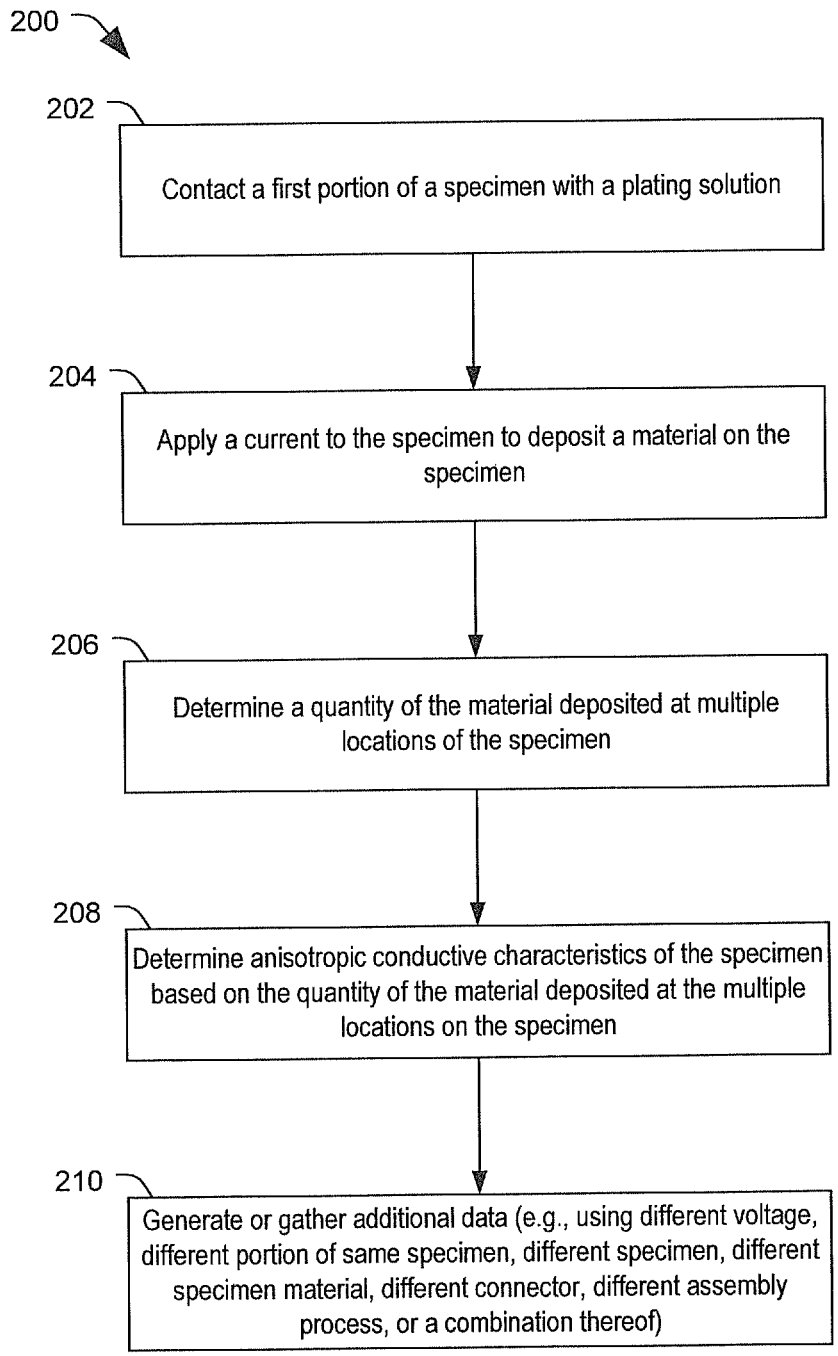
FIG. 2 is a flow chart of a particular embodiment of a method of determining anisotropic conductive characteristics of a specimen.

FIG. 2 is a flow chart of a particular embodiment of a method 200 of determining anisotropic conductive characteristics of a specimen (e.g., a specimen including a fiber-based composite, such as a carbon-fiber composite). For example, the specimen may include or correspond to the specimen 102 of FIG. 1. The method 200 includes, at 202, contacting a first portion of a specimen with a plating solution. For example, the first portion of the specimen may include at least portion of the first edge 114 of the specimen 102 of FIG. 1.

The method 200 also includes, at 204, applying a current to the specimen to deposit a material (e.g., copper or another metal) on the specimen. In a particular embodiment, the current is applied at a second portion of the specimen (e.g., a location that is proximate a center of the specimen), and the specimen anisotropically conducts the current from the second portion of the specimen to the first portion of the specimen (e.g., the edge of the specimen).

The method 200 also includes, at 206, determining a quantity of the material deposited at multiple locations of the specimen. The quantity of the material deposited at each location may be measured (e.g., using height-sensitive microscopy as described above) or estimated (e.g., based on color changes of the specimen) depending on desired accuracy of the determination. For example, the quantity of the material deposited at a particular location of the multiple locations may be determined using an optical measurement device to measure a height of a layer of the material deposited at the particular location.

The method 200 also includes, at 208, determining anisotropic conductive characteristics of the specimen based on the quantity of the material deposited at the multiple locations on the specimen. For example, determining the anisotropic conductive characteristics of the specimen may include estimating a current density distribution of a portion of the specimen responsive to the current. To illustrate, a high current density distribution at a particular location of the specimen may be indicated by a larger quantity of the material deposited at the particular location.

The method 200 may also include, at 210, generating or gathering additional data. Specific examples of generating or gathering additional data are described with reference to flowcharts of FIGS. 3-8. The anisotropic conductive characteristics of the specimen, the additional data, or both, may be used to predict performance of a component formed of the composite material when the component is subjected to a lightning strike.

FIG. 3 is a flow chart of a first embodiment of a method 210 of generating or gathering additional data from FIG. 2.

In FIG. 3, the method 210 includes, at 302, generating a 2-dimensional map of a current density distribution at an edge of the specimen based on the quantity of the material deposited at the multiple locations on the specimen. For example, a map of the current density distribution may be generated for an area of the specimen corresponding to a thickness of the specimen and at least a portion of the edge that is contacted with the plating solution. The 2-dimensional map of a current density distribution may provide information regarding anisotropic current flow to the edge of the specimen.

FIG. 4 is a flow chart of a second embodiment of a method 210 of generating or gathering additional data from FIG. 2. In FIG. 4, the method 210 includes, at 402, after determining the quantity of the material deposited at multiple locations of the specimen, removing at least a section of the first edge of the specimen to form a second edge of the specimen. For example, a portion of the specimen 102 of FIG. 1 may be removed (e.g., cut away) to expose the second edge 116.

The method 210 may also include, at 404, contacting a portion of the specimen (including the second edge) with the plating solution, and, at 406, applying a second current to the specimen to deposit the material on the specimen at the second edge. The method 210 may further include, at 408, determining a second quantity of the material deposited at multiple locations of the second edge of the specimen and, at 410, determining second anisotropic conductive characteristics of the specimen based on the quantity of the material deposited at the multiple locations on the second edge.

The method 210 may also include, at 412, generating a 3-dimensional map of a current density distribution of the specimen based on the anisotropic conductive characteristics and the second anisotropic conductive characteristics. For example, multiple 2-dimensional maps, each corresponding to a different circumferential edges of the specimen, may be combined to make the 3-dimensional map of the current density distribution. The 3-dimensional map of the current density distribution may provide information regarding anisotropic current flow from proximate a center of the specimen to multiple circumferential edges of the specimen, in effect, describing anisotropic current distribution within a body of the specimen.

Figure 5:
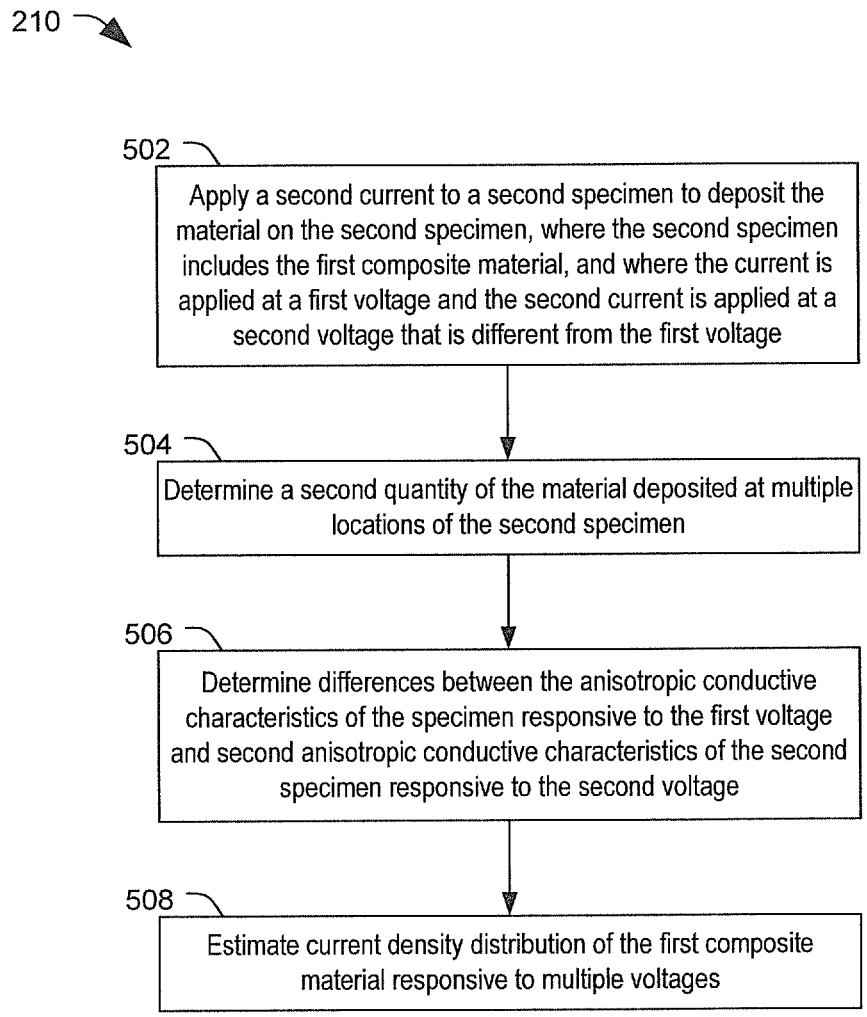
FIG. 5 is a flow chart of a third embodiment of a method of generating or gathering additional data from FIG. 2.

FIG. 5 is a flow chart of a third embodiment of the method 210 of generating or gathering additional data from FIG. 2. The method 210 of FIG. 5 may include contacting a second specimen with a plating solution and, at 502, applying a second current to the second specimen to deposit the material on the second specimen. The second specimen may be formed of the same material as the specimen. For example, the specimen may include a first composite material and the second specimen may include the first composite material. The second current may be applied at a second voltage, which may be different than a voltage (e.g., a first voltage) used to apply the current to the specimen.

The method 210 also includes, at 504, determining a second quantity of the material deposited at multiple locations of the second specimen, and, at 506, determining differences between the anisotropic conductive characteristics of the specimen responsive to the first voltage and anisotropic conductive characteristics of the second specimen responsive to the second voltage. The method 210 may also include, at 508, estimating current density distribution of the first composite material responsive to multiple voltages. For example, a current-voltage relationship of the first composite material may be determined.

Figure 6:
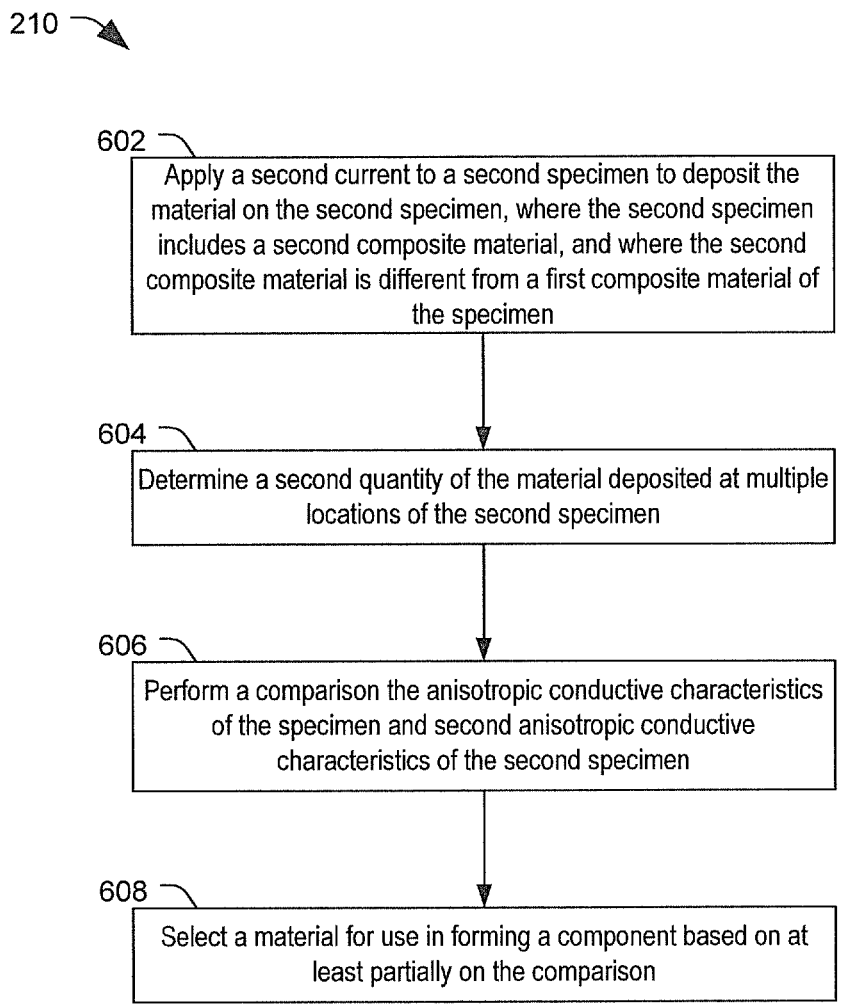
FIG. 6 is a flow chart of a fourth embodiment of a method of generating or gathering additional data from FIG. 2.

FIG. 6 is a flow chart of a fourth embodiment of the method 210 of generating or gathering additional data from FIG. 2. The method 210 of FIG. 6 may include contacting a second specimen with a plating solution and, at 602, applying a second current to the second specimen to deposit the material on the second specimen. The second specimen may be formed of a different material than the specimen. For example, the specimen may include a first composite material and the second specimen may include a second composite material that is different from the first composite material.

The method 210 may also include, at 604, determining a second quantity of the material deposited at multiple locations of the second specimen. The method 210 may also include, at 606, performing a comparison the anisotropic conductive characteristics of the specimen and anisotropic conductive characteristics of the second specimen, and, at 608, selecting a material for use in forming a component based on at least partially on the comparison. For example, a current density distribution of the specimen may be compared to a current density distribution of the second specimen. The first composite material or the second composite material may be selected to be used to form a component (such as an aircraft skin panel or a test panel to be subject to lightning strike testing) based on the comparison. To illustrate, the particular composite material that is associated with a more uniform current density distribution may be selected.

Figure 7:
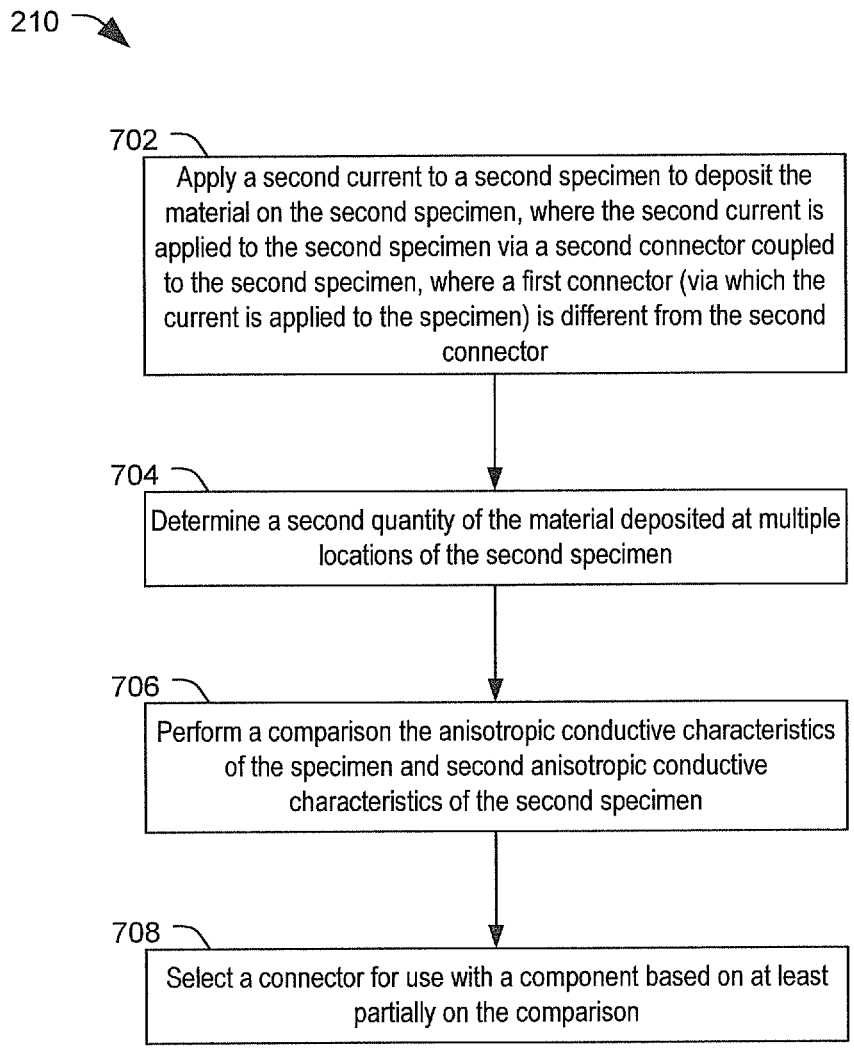
FIG. 7 is a flow chart of a fifth embodiment of a method of generating or gathering additional data from FIG. 2.

FIG. 7 is a flow chart of a fifth embodiment of the method 210 of generating or gathering additional data from FIG. 2. The method 210 of FIG. 7 may include contacting a second specimen with a plating solution and, at 702, applying a second current to a second specimen to deposit the material on the second specimen. The second specimen may be formed of the same material as the specimen or may be formed of a different material. A second connector used to apply the second current to the second specimen may be different than a first connector used to apply the current to the specimen. For example, the first and second connectors may be of different types (e.g., a rivet rather than a threaded fastener), may be formed of different materials, may be of different sizes and/or shapes, may differ in another manner (e.g., thread count or thread pitch), or a combination thereof.

The method 210 may also include, at 704, determining a second quantity of the material deposited at multiple locations of the second specimen. The method 210 may further include, at 706, performing a comparison the anisotropic conductive characteristics of the specimen and second anisotropic conductive characteristics of the second specimen, and, at 708, selecting a connector for use with a component based on at least partially on the comparison. For example, a current density distribution of the specimen (using the first connector) may be compared to a current density distribution of the second specimen (using the second connector). A particular connector may be selected to be used to form a component (such as an aircraft skin panel or a test panel to be subject to lightning strike testing) based on the comparison. To illustrate, the particular connector that is associated with a more uniform current density distribution may be selected.

Figure 8:
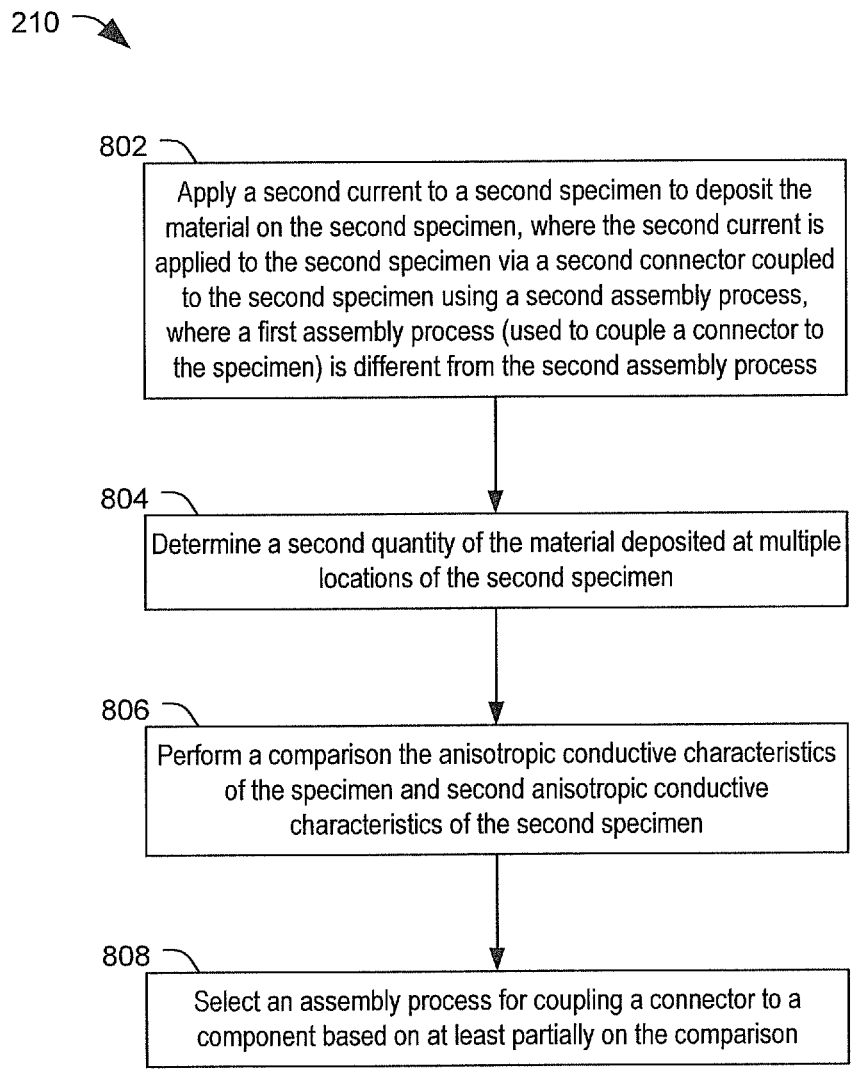
FIG. 8 is a flow chart of a sixth embodiment of a method of generating or gathering additional data from FIG. 2.

FIG. 8 is a flow chart of a sixth embodiment of the method 210 of generating or gathering additional data from FIG. 2. The method 210 of FIG. 8 may include contacting a second specimen with a plating solution and, at 802, applying a second current to a second specimen to deposit the material on the second specimen. The second specimen may be formed of the same material as the specimen or may be formed of a different material. A second assembly process used to form the second specimen (e.g., to couple a second connector to the second specimen) may be different than a first assembly process used to form the specimen (e.g., to couple a first connector to the specimen). For example, the first and second assembly processes may use different types connector interfaces or different connector interface materials, may use different sizes and/or shapes of connector interfaces, may differ in another manner (e.g., a curing temperature of a connector interface material), or a combination thereof.

The method 210 may also include, at 804, determining a second quantity of the material deposited at multiple locations of the second specimen. The method 210 may further include, at 806, performing a comparison the anisotropic conductive characteristics of the specimen and second anisotropic conductive characteristics of the second specimen, and, at 808, selecting an assembly process for coupling a connector to a component based on at least partially on the comparison. For example, a current density distribution of the specimen (using the first assembly process) may be compared to a current density distribution of the second specimen (using the second assembly process). A particular assembly process may be selected to be used to form a component (such as an aircraft skin panel or a test panel to be subject to lightning strike testing) based on the comparison. To illustrate, the particular assembly process that is associated with a more uniform current density distribution may be selected.

Although various methods 210 of gathering or generating additional data have been described with reference to FIGS. 3-8, these methods 210 should not be understood to be mutually exclusive alternatives. Rather, additional data may be gathered or generating using any two or more of the methods 210 of FIGS. 3-8 together. To illustrate, both a material and a connector to be used to form a component may be selected by combining methods 210 of FIGS. 6 and 7. As another illustrative example, a 2-dimensional map of current density distribution (determined using the method 210 of FIG. 3), a 3-dimensional map of current density distribution (determined using the method 210 of FIG. 4), or both, may be used to facilitate selection of a material, a component, and/or and assembly process to be used to form a component. Additionally, although each of the methods 210 of FIGS. 5-8 has been described in terms of two specimens, the methods may be performed using more than two specimens. For example, the method 210 of any of FIGS. 5-8 may repeated for a third specimen, a fourth specimen, or additional specimens, in order to compare more than two materials, more than two connectors, more than two assembly processes or more than two voltages. Likewise, although the method 210 of FIG. 4 is described for two edges, the method 210 of FIG. 4 may be repeated for additional edges to generate a more complete or more extensive 3-dimensional map.

Figure 9:
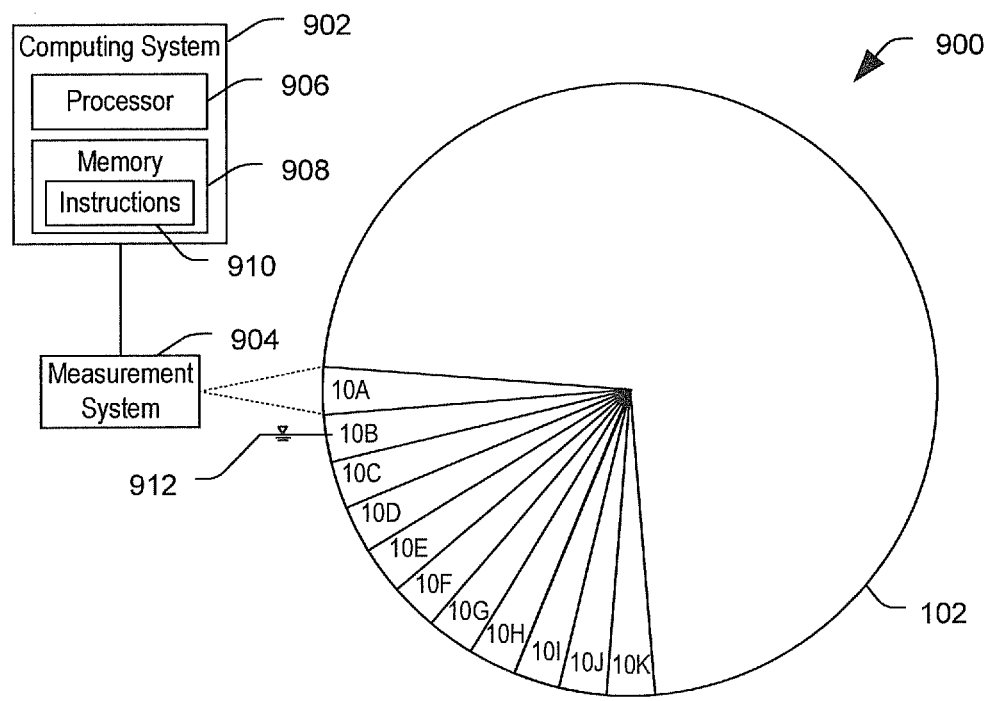
FIG. 9 is a diagram illustrating a system to evaluate anisotropic conductive characteristics of a specimen and illustrating approximate views corresponding to FIGS. 10A-10K.

FIG. 9 is a diagram illustrating a system 900 to evaluate anisotropic conductive characteristics of a specimen and illustrating approximate views corresponding to FIGS. 10A-10K. The system 900 includes a computing system 902 coupled to a measurement system 904. The system 900 also shows the specimen 102 after depositing a material on the specimen. An approximate fluid surface level during the deposition process is designated 912 to facilitate description of FIGS. 10A-10K.

The measurement system 904 may be configured to measure a parameter corresponding to a quantity of material deposited at a particular location of the specimen 102. For example, the measurement system 904 may include an optical measurement device that is capable of determining the quantity of material deposited at a particular location of the specimen 102 based on color difference of the specimen 102, based on a height of a deposited layer, based on other information, or a combination thereof. The measurement system 904 may provide data corresponding to the measured parameter (e.g., a value indicating the height of the deposited layer) to the computing system 902.

The computing system 902 may include a processor 906 and a memory 908 (e.g., a non-transitory computer-readable storage device). The memory 908 may store instructions 910 that are executable by the processor 902 to perform calculation, analysis, evaluation or determination processes associated with the methods of one or more of FIGS. 2-8. For example, the processor 902 may execute the instructions 910 to receive data indicating a measured parameter from the measurement system 904 and may determine a quantity of the material deposited at a particular location of the specimen 102 based on the data. As another example, the processor 902 may execute the instructions 910 to generate a 2-dimensional or 3-dimensional map of current density distribution for the specimen 102 based on the quantity of the material deposited at the multiple locations on the specimen 102.

In a particular embodiment, the measurement system 904 measures the measured parameter at one location of specimen at a time. For example, as illustrated in FIG. 9, the measurement system 904 and the specimen 102 are oriented to enable the measurement system 904 to measure the parameter at an edge of the specimen within an arc angle designated 10A. Subsequently, the measurement system 904 and/or the specimen 102 may be re-oriented to enable the measurement system 904 to measure the parameter at the edge of the specimen at another location (corresponding to another arc angle), such as one or more of the arc angles designated 10B-10K. As described above, after measuring multiple locations of the specimen, the edge of the specimen may be removed to reveal a new edge. Material may be deposited on the new edge, and the measurement system 904 may be used to measure the parameter at various locations on the new edge.

Figure 10A:
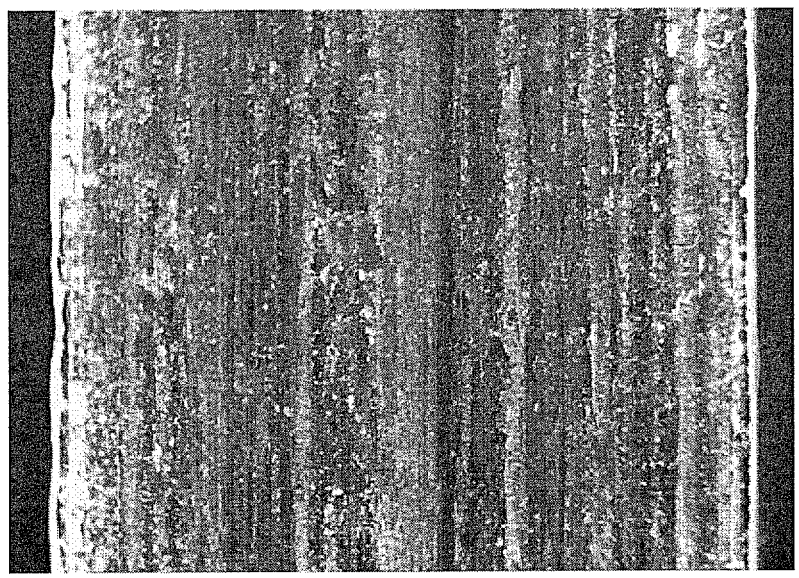
FIGS. 10A-10K each illustrate an image of a portion of an edge of a specimen after electroplating.
Figure 10B:
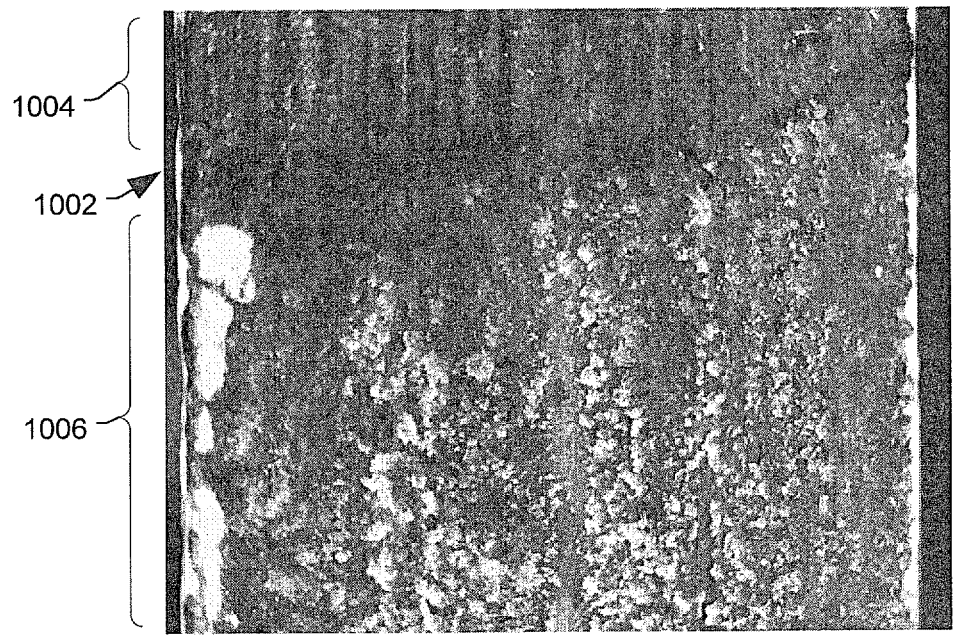
Figure 10C:
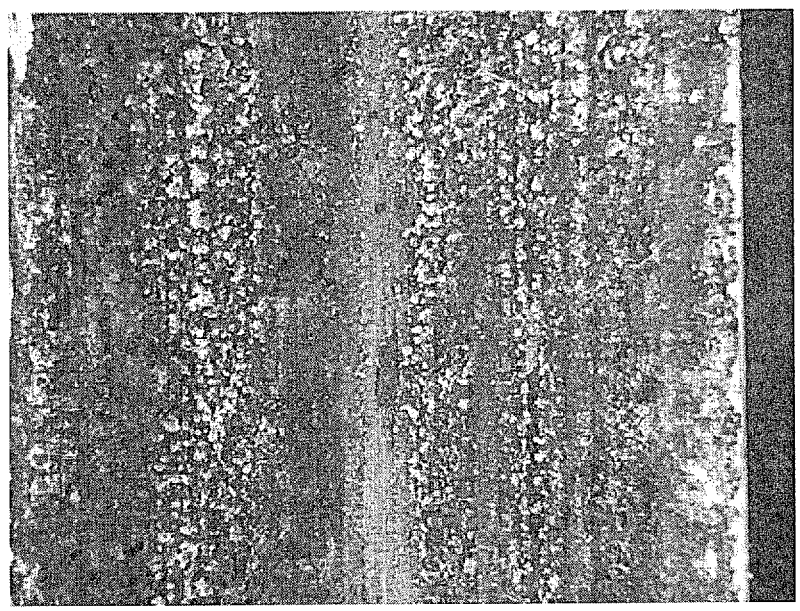
Figure 10D:
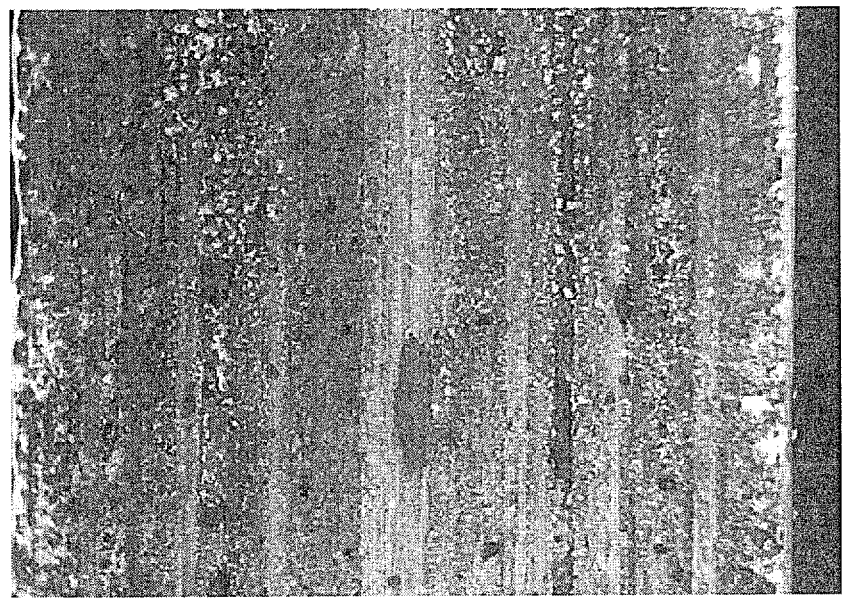
Figure 10E:
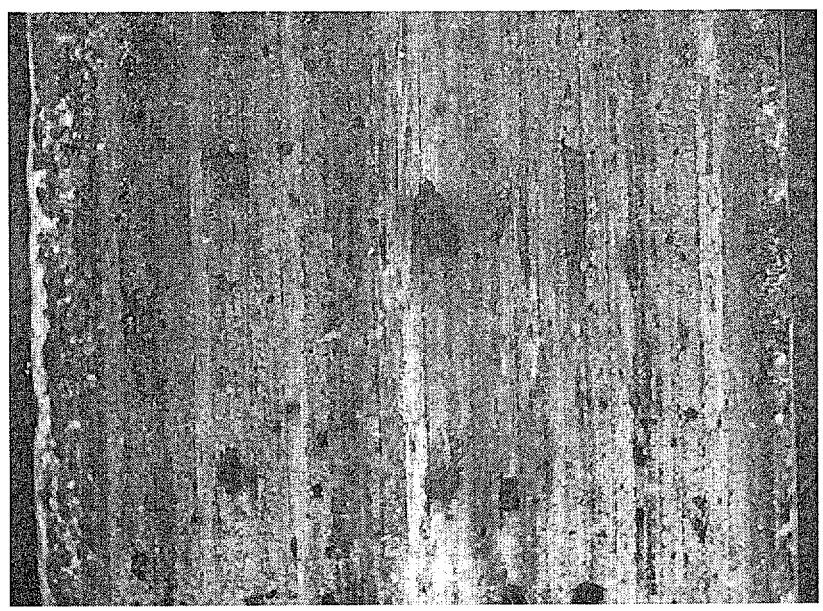
Figure 10F:
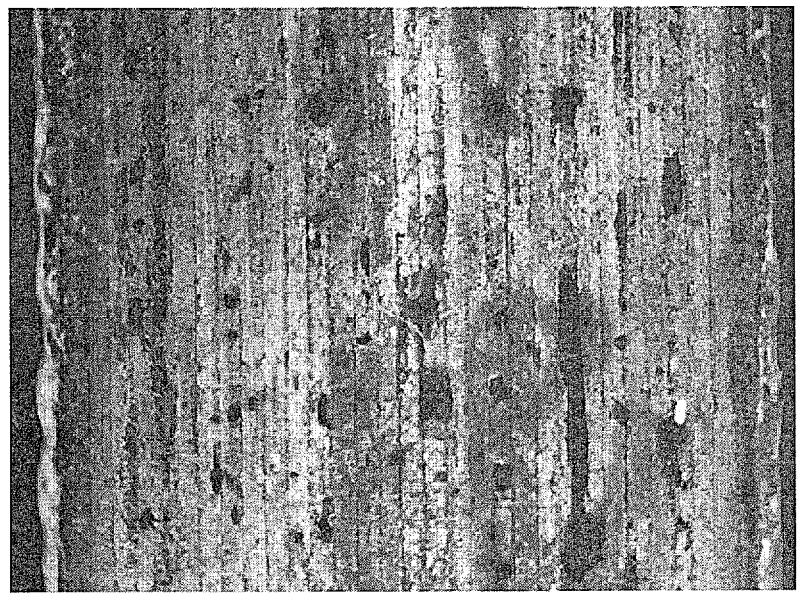
Figure 10G:
Figure 10H:
Figure 10I:
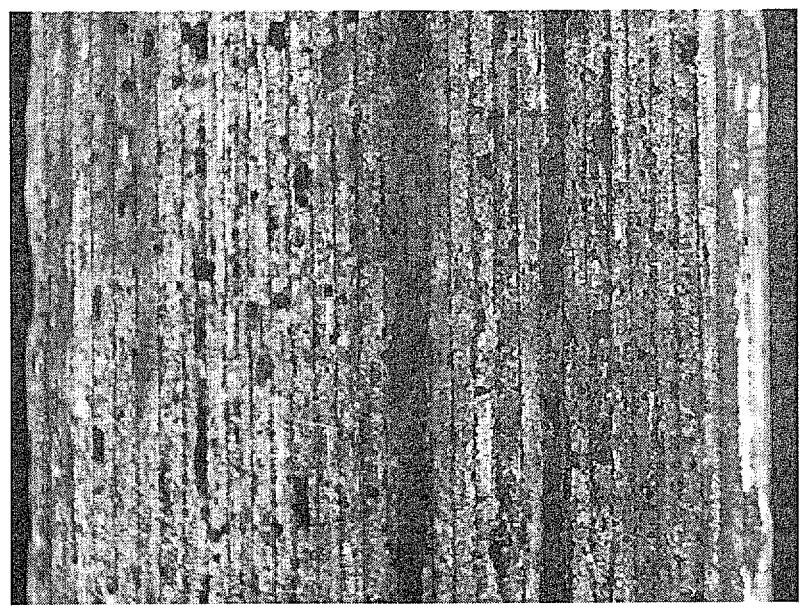
Figure 10J:
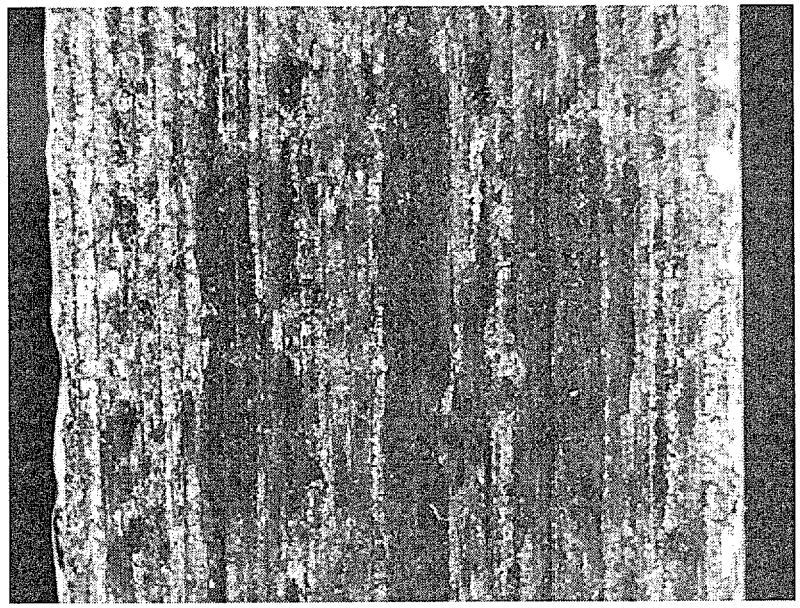
Figure 10K:
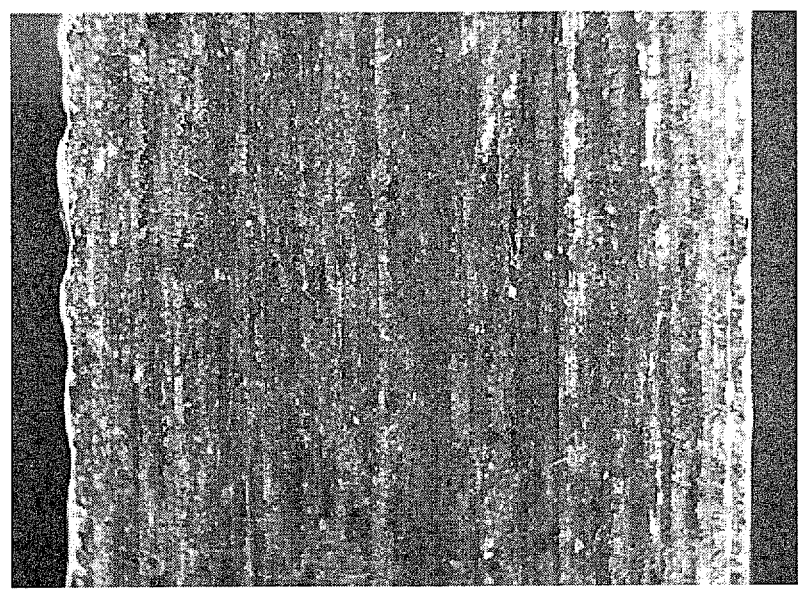

FIGS. 10A-10K each illustrates an image of a portion of an edge of a specimen after electroplating. The images in FIGS. 10A-10K correspond to the arc angles designated 10A-10K in FIG. 9. For example, FIG. 10A shows a microscopic image of a first portion of an edge of the specimen 102 at the arc angle 10A of FIG. 9. Likewise, FIG. 10B shows a microscopic image of a second portion of the edge of the specimen 102 at the arc angle 10B of FIG. 9.

As shown in FIG. 9, the first portion of the edge of the specimen in FIG. 10A was above the fluid surface level 912 during the deposition process. Accordingly, the microscopic image in FIG. 10A shows only the edge of the specimen with no material deposited on the edge.

FIG. 10B shows a portion of the edge of the specimen that crosses the fluid surface level 912 of the plating solution in FIG. 9. In FIG. 10B, an approximate location of the fluid surface level 912 is visible at interface location 1002. Above the interface location 1002 (e.g., in an area designated 1004), the specimen is unplated (e.g., no material has been deposited). Below the interface location 1002 (e.g., in an area designated 1006), material was deposited on the specimen and shows up in the image of FIG. 10B as gray or white areas (depending a quantity of the material deposited).

Material deposited on the specimen is also visible in FIGS. 10C-10K as varying shades of gray and white depending on the quantity of the material deposited. Plies of the specimen are also visible in at least some of the images. For example, plies of the specimen are visible in FIGS. 10H and 10I. Accordingly, FIGS. 10B-10K illustrate how the quantity of material deposited on the specimen can vary by location (e.g., by arc angle) on the specimen. Of course, FIGS. 10A-10K illustrate results for only a particular specimen subjected to the methods described above. Subjecting other specimens to the methods described above would be expected to result in different quantities and distributions to material deposited. Since the quantity and distribution of material deposited is related to current density distribution of each specimen tested, the current density distribution of various specimens can be compared. For example, a visual or optical examination may provide a rough comparison of the current density distribution. A more detailed comparison of the current density distribution may be determined by quantifying the material deposited at various location of each specimen.

Figure 11:
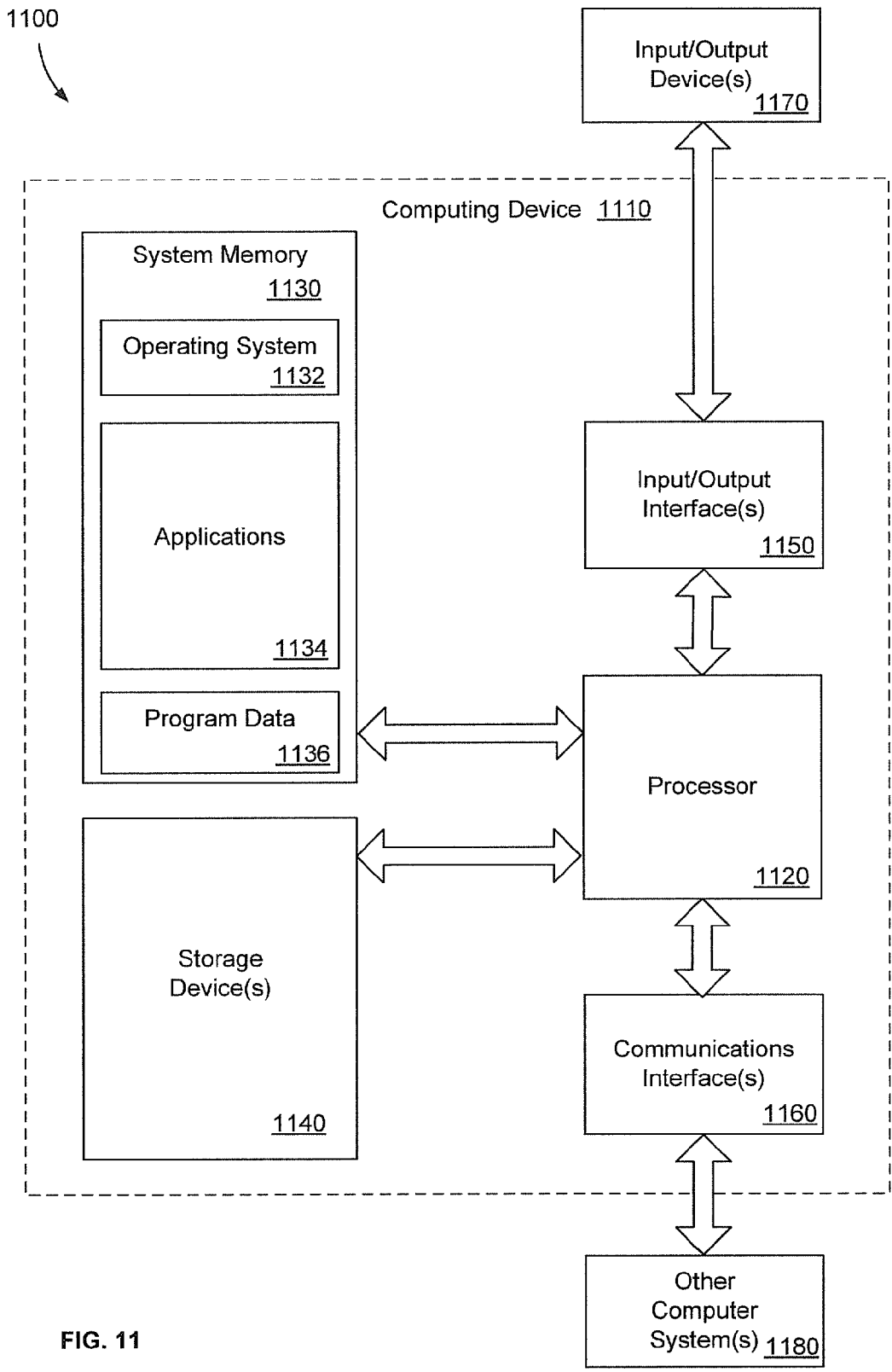
FIG. 11 is a block diagram of an illustrative embodiment of a computing device that may be used to evaluate anisotropic conductive characteristics of a specimen.

FIG. 11 is a block diagram of an illustrative embodiment of a computing environment 1100 that may be used to evaluate anisotropic conductive characteristics of a specimen. The environment 1100 including a general purpose computing device 1110 to support embodiments of computer-implemented methods and computer-executable program instructions (or code) according to the present disclosure. For example, the computing device 1110, or portions thereof, may execute instructions to analyze anisotropic conductive characteristics of a specimen (e.g., based on measurements of a quantity of material deposited on the specimen at various locations). In a particular embodiment, the computing device 1110 may include, be included with, or correspond to the computing system 902 of FIG. 9.

The computing device 1110 may include a processor 1120. The processor 1120 may communicate with a system memory 1130, one or more storage devices 1140, one or more input/output interfaces 1150, one or more communications interfaces 1160, or a combination thereof. The system memory 1130 may include volatile memory devices (e.g., random access memory (RAM) devices), nonvolatile memory devices (e.g., read-only memory (ROM) devices, programmable read-only memory, and flash memory), or both. The one or more storage devices 1140 may include nonvolatile storage devices, such as magnetic disks, optical disks, or flash memory devices. The storage devices 1140 may include both removable and non-removable memory devices. In a particular embodiment, the system memory 1130, the storage devices 1140, or both, include tangible, non-transitory computer-readable media.

The system memory 1130, the one or more storage devices 1140, or both, may include an operating system 1132, which may include a basic/input output system for booting the computing device 1110 as well as a full operating system to enable the computing device 1110 to interact with users, other programs, and other devices. The system memory 1130, the one or more storage devices 1140, or both, may include one or more application programs 1134, such as an application to analyze or compare anisotropic conductive characteristics of one or more specimens (e.g., based on measurements of a quantity of material deposited on the specimen(s) at various locations), instructions to generate a multidimensional map of the conductive characteristics of a specimen, instructions to perform or facilitate performance of one or more of the methods of FIGS. 2-8, or a combination thereof. The system memory 1130, the one or more storage devices 1140, or both, may include program data 1136, such as results generated by the one or more applications 1134 or operating data used by the one or more applications 1134. For example, the program data 1136 may include data corresponding to anisotropic conductive characteristics of one or more specimens, a multidimensional map of the conductive characteristics of the one or more specimens, other data resulting from performance of one or more of the methods of FIGS. 2-8, or a combination thereof.

The processor 1120 may also communicate with one or more input/output interfaces 1150 that enable the computing device 1110 to communicate with one or more input/output devices 1170 to facilitate user interaction. The input/output interfaces 1150 may include serial interfaces (e.g., universal serial bus (USB) interfaces or Institute of Electrical and Electronics Engineers (IEEE) 1394 interfaces), parallel interfaces, display adapters, audio adapters, and other interfaces. The input/output devices 1170 may include keyboards, pointing devices, displays, speakers, microphones, touch screens, a measurement system (such as the measurement system 904 of FIG. 9), other devices, or a combination thereof. The processor 1120 may detect interaction events based on user input received via the input/output interfaces 1150. Additionally, the processor 1120 may send a display (e.g., one or more of the images of FIGS. 10A-10K, a multidimensional map of conductive characteristics of a specimen, a numerical or graphical comparison of conductive characteristics of two or more specimens, etc.) to a display device via the input/output interfaces 1150.

The processor 1120 may communicate with other computer systems 1180 via the one or more communications interfaces 1160. The one or more communications interfaces 1160 may include wired Ethernet interfaces, IEEE 802 wireless interfaces, other wireless communication interfaces, or other network interfaces. The other computer systems 1180 may include host computers, servers, workstations, and other computing devices.

Embodiments described above are illustrative and do not limit the disclosure. It is to be understood that numerous modifications and variations are possible in accordance with the principles of the present disclosure.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it is to be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to fewer than all of the features of any of the disclosed embodiments.

What is claimed is:

1. A method for determining anisotropic conductive characteristics of a specimen, comprising:
applying a first current to a specimen to deposit a material on the specimen, the specimen including a first composite material;
determining a quantity of the material deposited at a first set of multiple locations on an edge of the specimen, wherein determining the quantity at a particular location of the first set of multiple locations includes measuring a height of a layer of the material deposited at the particular location;
determining anisotropic conductive characteristics of the specimen based on the quantity of the material deposited at the first set of multiple locations on the specimen, wherein determining the conductive characteristics includes estimating a current density distribution of a portion of the specimen responsive to the first current;
applying a second current to a second specimen to deposit the material on the second specimen, wherein the second specimen includes a second composite material, and wherein the second composite material is different from the first composite material;
determining a second quantity of the material deposited at a second set of multiple locations of the second specimen;
performing a comparison of the anisotropic conductive characteristics of the specimen and second anisotropic conductive characteristics of the second specimen; and
based on the anisotropic conductive characteristics of the specimen, predicting performance of a component formed of the first composite material and the second composite material.

2. The method of claim 1, wherein the specimen includes a carbon-fiber composite.

3. The method of claim 1, wherein the material includes copper.

4. The method of claim 1, wherein determining the quantity of the material deposited at the particular location of the first set of multiple locations includes using an optical measurement device to measure the height of the layer of the material deposited at the particular location.

5. The method of claim 1, further comprising contacting a first portion of the specimen with a plating solution before applying the first current, wherein the first current is applied at a second portion of the specimen, and wherein the specimen anisotropically conducts the first current from the first portion of the specimen to the second portion of the specimen.

6. The method of claim 5, wherein the first portion of the specimen includes a first edge of the specimen and the second portion of the specimen is proximate a center of the specimen.

7. The method of claim 6, further comprising, after determining the quantity of the material deposited at multiple locations of the specimen:
removing at least a section of the first edge of the specimen to form a second edge of the specimen;
contacting a portion of the specimen with the plating solution;
applying a third current to the specimen to deposit the material on the specimen at the second edge;
determining a third quantity of the material deposited at a third set of multiple locations of the second edge of the specimen; and
determining third anisotropic conductive characteristics of the specimen based on the quantity of the material deposited at the third set of multiple locations on the second edge.

8. The method of claim 7, further comprising generating a 3-dimensional map of a current density distribution of the specimen based on the anisotropic conductive characteristics and the third anisotropic conductive characteristics.

9. The method of claim 1, wherein applying the first current comprises applying a first voltage to the specimen, wherein applying the second current to the second specimen comprises applying a second voltage to the second specimen, and wherein the first voltage is different from the second voltage.

10. The method of claim 1, wherein determining the anisotropic conductive characteristics includes generating a two dimensional map of a current density distribution associated with the specimen, and further comprising:
selecting a material for use in forming a component based on at least partially on the comparison.

11. The method of claim 1, wherein the first current is applied to the specimen via a first connector coupled to the specimen, wherein the second current is applied to the second specimen via a second connector coupled to the second specimen, wherein the first connector is different from the second connector, and further comprising
selecting a connector for use with a component based at least partially on the comparison.

12. The method of claim 1, wherein the first current is applied to the specimen via a first connector that is coupled to the specimen using a first assembly process, wherein the second current is applied to the second specimen via a second connector coupled to the second specimen using a second assembly process, wherein the first assembly process is different from the second assembly process, and further comprising
selecting an assembly process for coupling the first connector or the second connector to a component based at least partially on the comparison, the component including the first composite material.

13. The method of claim 12, wherein the first connector is different from the second connector.

14. The method of claim 12, wherein the first assembly process includes using a first interface material between the first connector and the specimen and the second assembly process includes using a second interface material between the second connector and the second specimen, wherein the first interface material is different from the second interface material.

15. A method for determining anisotropic conductive characteristics of a specimen, comprising:
after contacting a first portion of a first edge of a specimen with a plating solution, applying a first current to a portion of the specimen to deposit a material on the specimen;
determining a first quantity of the material deposited at a first location of the first portion of the specimen;
determining first anisotropic conductive characteristics of the specimen based on the first quantity of the material;
after determining the first quantity:

removing at least a section of the first edge of the specimen to form a second edge of the specimen;

after contacting a second portion of the second edge with the plating solution, applying a second current to the specimen to deposit the material on the specimen at the second edge;

determining a second quantity of the material deposited at a second location of the second edge of the specimen; and determining second anisotropic conductive characteristics of the specimen based on the second quantity of the material; and outputting information related to performance of a component formed of the material, the information based on at least one of the first anisotropic conductive characteristics of the specimen and the second anisotropic conductive characteristics of the specimen.

16. The method of claim 15, wherein the second portion of the specimen is proximate to a center of the specimen, wherein determining the quantity at the first location includes measuring a first height of a layer of the material deposited at the first location, and wherein the specimen anisotropically conducts the first current from the first portion of the specimen to the second portion of the specimen.

17. The method of claim 15, wherein determining the first anisotropic conductive characteristics includes generating a two dimensional map of a current density distribution of the first edge of the specimen based on the material deposited at the first location.

18. A method for determining anisotropic conductive characteristics of a specimen, comprising:

applying a first voltage to a specimen to induce a first current at the specimen, the first current associated with deposition of a material on the specimen, wherein the specimen includes a composite material;

determining a quantity of the material deposited at multiple locations on an edge of the specimen;

determining anisotropic conductive characteristics of the specimen based on the quantity of the material deposited at the multiple locations on the specimen;

applying a second voltage to a second specimen to induce a second current at the second specimen, the second current associated with deposition of the material on the second specimen, wherein the second specimen includes the composite material, and wherein the second voltage that is different from the first voltage;

determining a second quantity of the material deposited at multiple locations of the second specimen;

determining second anisotropic conductive characteristics of the second specimen based on the second quantity of the material deposited at the multiple locations on the second specimen; and estimating a current density distribution of the composite material based on the first voltage and the second voltage.

19. The method of claim 18, further comprising determining one or more differences between the anisotropic conductive characteristics of the specimen and the second anisotropic conductive characteristics of the second specimen.

20. The method of claim 19, wherein the current density distribution is estimated based on the one or more differences, and wherein the specimen includes a carbon-fiber composite.

* * * * *